United States Patent
Cuomo et al.

(10) Patent No.: US 8,701,478 B2
(45) Date of Patent: Apr. 22, 2014

(54) METHODS AND DEVICES FOR TESTING BLOW-OUT PANELS

(71) Applicant: Alenia Aermacchi S.p.A., Venegono Superiore (IT)

(72) Inventors: Salvatore Cuomo, Venegono Superiore (IT); Graziano Capone, Venegono Superiore (IT); Igino Covino, Venegono Superiore (IT); Francesco Rainone, Venegono Superiore (IT); Biagio De Maio, Venegono Superiore (IT)

(73) Assignee: Alenia Aermacchi S.p.A., Venegono Superiore (VA) (IT)

( * ) Notice: Subject to any disclaimer, the term of this patent is extended or adjusted under 35 U.S.C. 154(b) by 0 days.

(21) Appl. No.: 13/689,834

(22) Filed: Nov. 30, 2012

(65) Prior Publication Data

US 2013/0133414 A1     May 30, 2013

(30) Foreign Application Priority Data

Nov. 30, 2011    (IT) .............................. TO2011A1099

(51) Int. Cl.
     *G01M 99/00*      (2011.01)
(52) U.S. Cl.
     USPC ....................................................... 73/118.03
(58) Field of Classification Search
     USPC ....................................................... 73/118.03
     See application file for complete search history.

(56) References Cited

U.S. PATENT DOCUMENTS

| | | | |
|---|---|---|---|
| 2,525,345 A | 10/1950 | Getchell | |
| 2,826,063 A | 3/1958 | Astley | |
| 2,907,200 A | 10/1959 | Roberts et al. | |
| 3,580,050 A | 5/1971 | Waldron | |
| 3,600,940 A | 8/1971 | Schlegel | |
| 3,875,789 A * | 4/1975 | Orosy | 73/40 |
| 3,958,448 A | 5/1976 | Willis et al. | |
| 4,282,744 A * | 8/1981 | Dick | 73/49.3 |
| 4,395,917 A | 8/1983 | Maltby, Jr. et al. | |
| 4,715,215 A * | 12/1987 | Perhach et al. | 73/49.3 |
| 4,967,602 A | 11/1990 | Norton | |
| 5,424,634 A | 6/1995 | Goldfarb et al. | |
| 5,992,242 A | 11/1999 | Murphy et al. | |

FOREIGN PATENT DOCUMENTS

EP      1443317 A2    8/2004

\* cited by examiner

*Primary Examiner* — Freddie Kirkland, III
(74) *Attorney, Agent, or Firm* — Robert E. Alderson, Jr.

(57) ABSTRACT

Blow-out testing devices which include a box-like housing defining two contiguous inner chambers communicating directly with one another through an inner aperture which is closable by applying a blow-out panel thereupon are provided. In such devices at least one of the two chambers is provided with a hermetically closable door. Both chambers are pressurized and sealed. Opening the door, an instant pressure drop is caused in one of the two chambers. The pressure within the other chamber causes the panel to break. Methods for blow-out testing are also provided.

12 Claims, 1 Drawing Sheet

METHODS AND DEVICES FOR TESTING BLOW-OUT PANELS

CROSS REFERENCE TO RELATED APPLICATION

This application claims priority to and benefit of Italian Patent Application No. TO2011A001099 filed Nov. 30, 2011, the contents of which are incorporated by reference in their entirety.

FIELD OF THE INVENTION

The present invention relates to test devices and methods for testing blow-out panels.

BACKGROUND OF THE INVENTION

As known, pressurized civil aircraft are equipped with special systems aiming at reducing pressure peaks which are generated in the event of a rapid decompression which may weaken the fuselage structure. Such systems include blow-out panels that open at a certain value of differential pressure. The qualification and/or certification of the system is done through testing.

In the field of aeronautics, the blow-out panels are applied on decompression apertures in bulkheads separating two different environments. Should an excessive and potentially harmful pressure difference occur on the opposite sides of the bulkhead, for example, because of a gash in the fuselage, the blow-out panels are opened. This allows for a load compensation due to the pressure difference and prevent the entire bulkhead in which the panel is mounted from collapsing. On some aircrafts, blow-out panels are mounted on the floor, separating the Cargo Compartment Area and the EE-Bay Area. By tearing open, they prevent the floor from collapsing in the event of rapid decompression in one of the two environments. In other applications blow-out panels are mounted on the door that divides the cockpit from the cargo area, or on the bulkhead that separates the upper deck from the main deck.

Heretofore, tests on blow-out panels were mainly carried out with rather complex and expensive equipment. Such equipment typically makes use of a test cylinder of large size, about 5-6 m long with a diameter of about 60 cm, inside of which a vacuum is created by means of a vacuum machine. The panel to be tested is mounted adjacent to one of the end walls of the cylinder. The differential between the atmospheric pressure of the external environment and the vacuum in the cylinder causes the panel to break. The performance of the panel during its opening is studied by analyzing frames taken with a high speed digital camera.

SUMMARY OF THE INVENTION

It is therefore an object of the present invention to provide test devices for blow-out panels, mainly addressing the problem of optimizing and reducing the overall size of the apparatus and its costs.

Representative embodiments of the invention will now be described, by way of non-limiting examples along with the accompanying drawings.

DETAILED DESCRIPTION

Figure 1:
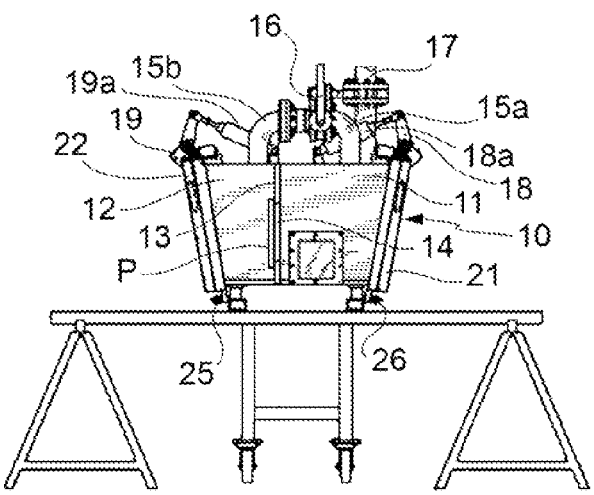
FIG. 1 is a cross sectional, elevation view of one embodiment of an apparatus according to an embodiment of the invention in a first operating condition.

With reference to the drawings, the testing apparatus comprises an outer housing 10, of rigid material, preferably metal, inside which there are defined two contiguous inner chambers 11, 12, separated by a partition 13. The partition has an internal aperture 14 which may be closed by applying thereto a blow-out panel P to be tested. Blow-out panels are known in the art and therefore need not be described in detail herein.

The shape and size of the partition 13 and the inner aperture 14, as well as those of the housing 10, are not essential for implementing the invention. In certain embodiments, in order to reduce the overall size of the apparatus and retain the panel adequately on the aperture 14, the partition 13 is configured as a flat frame which extends within the housing 10. In the illustrated example, the housing 10 is a box-like housing having an overall prismatic shape with a rectangular base, two vertical side walls, a top wall, a bottom wall and two opposite openable sides, vertical or inclined, as described herein. In certain embodiments the partition or frame 13 lies in a vertical plane.

The two chambers 11, 12 are in fluid communication with each other through an external connecting pipe comprising two tubular portions 15a, 15b which project each from a respective chamber 11, 12, and are mutually connected by means of a valve 16. The valve 16 serves to selectively establish or close a fluid communication between the two inner chambers 11, 12 through the connecting duct 15a, 15b. One of the two chambers (e.g. chamber 11) is connected directly to a source of pressurized air, for example a blower or a compressor (not shown), via a pressurized air inlet 17.

At least one of the two chambers 11, 12 may be put into communication with the outside through an opening 11a (FIG. 3) which is formed in an outer wall of the housing 10 and is hermetically closable. In certain embodiments, both chambers 11, 12 may be opened on the outside through a respective opening (only the opening 11a is visible in FIG. 3). The openings may be located in two outer walls, in this example in two opposite walls, of the housing 10. Each opening may be hermetically closable by a respective door 21, 22 which, when opened, puts the respective internal chamber 11, 12 in fluid communication with an outer ambient under the exterior of the device and thus at atmospheric pressure.

Each door 21, 22 may be associated with a respective quick opening device, selectively controllable to cause one of the two doors to open quickly. The quick opening device may include a latch mechanism 18, 19 associated with a quick release control 18a, 19a. In the illustrated example two bolt mechanisms 18, 19 are provided, each driven open by a respective control 18a, 19b, such as a pneumatic control.

Initially, the communication valve 16 between the two chambers is opened. Activating the blower, the two chambers are pressurized through the inlet 17. Upon reaching a predetermined pressure level inside the chambers, the communication valve 16 is closed. Subsequently, by acting on the pneumatic control associated with one of two latch mechanisms, the operator opens one of the two doors 21 or 22, instantaneously bringing the pressure in one of the two chambers to atmospheric pressure, in this example chamber 11. The pressure within chamber 12, and the sudden decompression in only one of the two chambers results in a corresponding pressure differential between the two chambers which, depending on the size and strength of the panel P being tested, causes an opening or crack in the panel P separating the environments of the two chambers.

In the particular embodiment illustrated, the doors of the apparatus are associated with thrust elements 24, which act between the outer body 10 and each door 21, 22, urging the doors towards their open positions. In the present example, the thrust elements 24 are helical springs that remain elastically compressed, in contrast to their elastic force, by the respective doors when these are locked in the closed position by the latch mechanisms. Due to the spring members, upon unlocking the latch, the spring of the door which is unlocked releases instantly, thus favoring a quick opening of the door.

Figure 2:
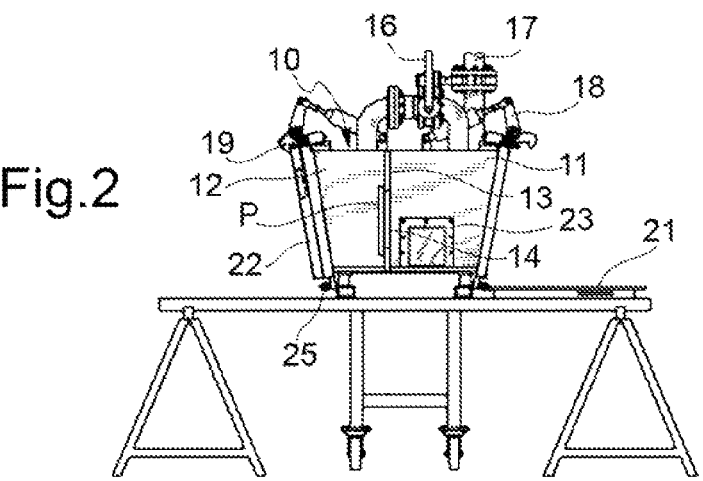
FIG. 2 is a view of the apparatus of FIG. 1, in a second operating condition.
Figure 3:
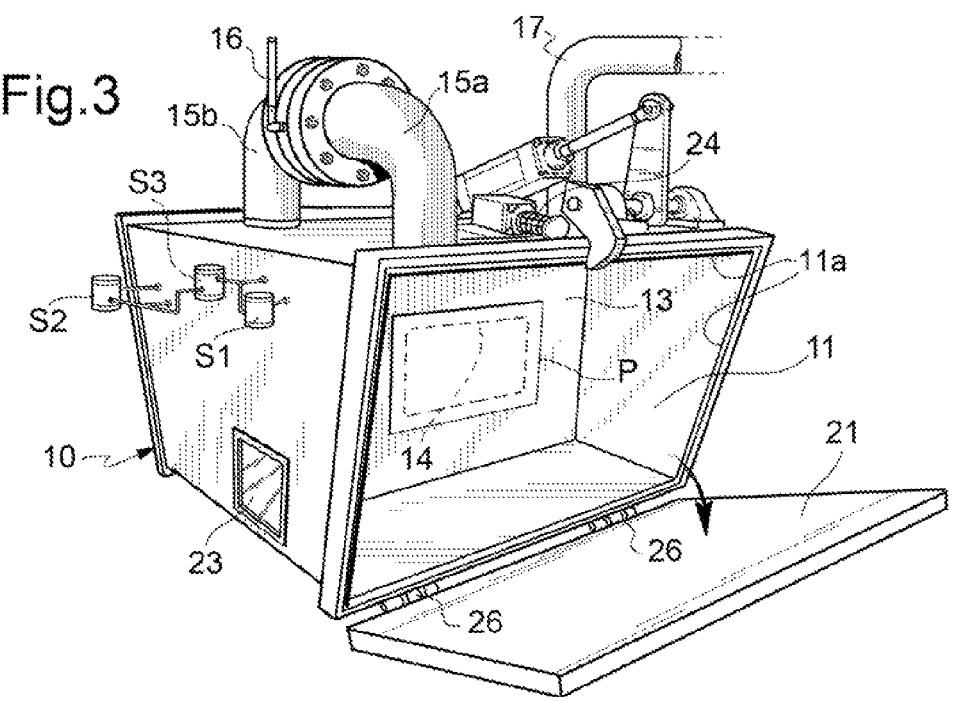
FIG. 3 is a schematic perspective view of the apparatus in the condition of FIG. 2.

In order to promote immediate opening of the selected door, it is preferably hinged at the bottom to the housing 10 with hinges or pivots 25, 26 along horizontal hinge axes. To ensure an even faster opening of the door, the openings 11a setting the inner chambers in communication with the outside and which are closed by doors 21, 22, are inclined with respect to a vertical plane, so that the top of the opening protrudes outwardly with respect to the lower part of the opening where the horizontal hinge axes are located. In this way, the unlocking of a selected latch leaves its door free to open by gravity, tilting downwards and outwards of the housing 10 (FIGS. 2 and 3).

The opening or breakage of the panel P being tested is monitored via pressure sensors schematically indicated S1-S3 which permits the measurement of the pressure in both chambers and the pressure differential between them. The pressure sensors may be mounted on the outside of the housing 10, and may include a first sensor S1 for measuring the pressure in chamber 11, a second sensor S2 for measuring the pressure in chamber 12, and a third sensor S3 that measures the pressure difference between the chambers 11 and 12. In the illustrated example the pressure sensors are connected pneumatically to the chambers through pressure taps PR1, PR2 provided on the housing 10 and hoses with fast-coupling connectors.

A system of microswitches may be used to measure the opening time of the panel being tested. Preferably four microswitches (not shown) are used, arranged in pairs. A first pair may be mounted in abutment on the panel P in a position in which it closes the inner aperture 14. The first pair of microswitches may be used to define the instant in which the panel starts to move under the effect of the pressure difference applied on its opposite side. The second pair of microswitches may be positioned at a predefined distance from the panel, in the opening direction, and can determine the instant when the panel intercepts the switches after covering the predefined distance. The time interval between these two instants represents the opening time of the panel. A high-speed digital camera may be used to photograph the test through a window 23. The apparatus can measure both the value of the minimum pressure difference that causes the panel to open and the opening speed. It should be noted that the present invention is not limited by the choice of the type or mode of application of the pressure sensors and microswitches, which may vary according to requirements.

The door (21 or 22) which opens to cause breakage of the panel P is selected depending on the direction in which the rupture is desired, that is, in collaboration with the pressure gradient that is created on opening the chosen door.

In the embodiment shown in FIG. 3, the panel P being tested is first constrained against one side of the partition 13, and then the door of the chamber towards which it is envisaged that the panel should break is opened. In other embodiments (not illustrated) the panel inside the apparatus may be secured in other ways, taking care to close the two chambers substantially in an airtight manner relative to one another by a partition wall, and that part of the partition wall includes the panel being tested, having two opposite faces which are each directly facing a respective one of the chambers.

The two opening doors allow performances of the tests in a bidirectional mode without having to move the panel being tested. The advantages of being able to carry out tests in a bidirectional mode can be appreciated in cases where the test panels being tested are designed so that they can break in either direction, foreseeing that the event of rapid decompression may occur either in chamber 11 or in chamber 12. When it is desired to test the capability of the panels to open in both directions it will be sufficient to open, in a first test session, the door 21 of chamber 11 and, in a second test session, the door 22 of chamber 12, without having to remove the panel being tested and fit it back on its opposite side, as is necessary with conventional test equipment.

The apparatus according to the present invention closely replicates the physical nature of the phenomenon reproducing a so-called "Sudden Decompression", since the sudden opening of one of the two doors (21 or 22) instantaneously reduces the pressure in the relative chamber down to the atmospheric pressure, whereas with conventional apparatus the simulation of the phenomenon is limited by the rate at which it is possible to create a vacuum (or decompression) in a chamber and thereby to provide the pressure difference able to break the panel being tested.

Those skilled in the art will recognize that the width of the opening and the door that opens it will be sufficient to cause a substantially instantaneous pressure drop in the inner chamber being opened, in order to closely simulate the conditions that, in flight, can produce the rupture of the panel P. In the illustrated example, the opening 11a has an width comparable to the size of the housing 10. In other embodiments, the opening 11a may be smaller. For example, the opening 11 may have a size comparable to that of the panel being tested test, or even smaller, for example with an area of the order of a few tens of square centimeters. The broadness of the opening must not be so small that it causes a gradual pressure drop in the inner chamber upon opening. A large opening also facilitates manual access to the partition 13 and makes it easy to apply or fix the panel to be tested over the inner aperture 14.

A further advantage accomplished by devices according to the present invention is the ability to reach values of differential pressure much higher than those that are achievable with conventional devices, the only limit being the sealing capability of the pressurizable chambers 11, 12. In the case of conventional devices working with vacuum, the maximum pressure differential with respect to the external environment is generally around 1 bar.

It will be appreciated that devices according to the present invention are economical, compact and simple, which allows manufacturers to perform complex tests on-sites both in development and certification/qualification which would otherwise be outsourced.

While a few exemplary embodiments have been disclosed in the foregoing detailed description, it should be appreciated that a large number of variations of the present invention exist. It should also be appreciated that the exemplary embodiments are only illustrative examples, and are not intended to limit the scope, applicability, or configuration in any way. Rather, the foregoing detailed description and the drawings will provide those skilled in the art with a convenient road map for implementing the invention, it being understood that various changes may be made in the function and arrangement of elements described in an exemplary embodiment without departing from the scope as set forth in the appended claims and their legal equivalents.

The invention claimed is:

1. A test apparatus for blow-out panels, comprising:
   a housing;
   two contiguous inner chambers, located within the housing, and communicating directly with one another through an inner aperture which is closable by applying a blow-out panel thereupon;
   a pressurized air inlet, communicating with at least one of the two chambers;
   a connecting duct which extends between the two inner chambers which is provided with a valve for selectively establishing or closing a fluid communication between the two chambers through said connecting duct;
   at least one opening, formed in an outer wall of the housing, the opening setting one of the two inner chambers in fluid communication with the exterior of the device at atmospheric pressure;
   at least one door hinged to the housing for hermetically closing the at least one opening;
   a quick opening device, associated with the door and operable to cause a rapid opening of the door, thereby causing a sudden difference in pressure between the two chambers and creating the conditions for the opening or rupture of the panel being tested.

2. The apparatus of claim 1, wherein both chambers are provided with a respective door which is hermetically closable and openable to put the respective chamber in fluid communication with the exterior of the device.

3. The apparatus of claim 1, wherein each door comprises a respective quick opening device.

4. The apparatus of claim 1, wherein the quick opening device comprises:
   a latch mechanism associated with a quick release control; and
   a thrust element, acting between the housing and the door, which forces the door toward an open position.

5. The apparatus of claim 4, wherein the quick release control comprises a pneumatic control.

6. The apparatus of claim 4, wherein the thrust element comprises a spring member.

7. The apparatus of claim 1, wherein the door is hinged at the bottom to the outer body with a horizontal hinge axis.

8. The apparatus of claim 7, wherein the opening lies on a plane inclined with respect to a vertical plane, so that a top part of the opening is situated more towards the outside of the housing with respect to a bottom part of the opening.

9. The apparatus of claim 1, wherein the connecting duct runs outside the housing and the valve is external to the housing.

10. The apparatus of claim 1, wherein the inner aperture is formed in a partition that extends within the housing and separates the two inner chambers from one another.

11. The apparatus of claim 1, wherein said opening and the door that closes it have a width such that, when the inner chamber closed by the door is pressurized, the opening of the door causes a substantially instantaneous pressure drop in the inner chamber to atmospheric pressure.

12. A method for testing blow-out panels, comprising:
   providing the test apparatus of claim 1;
   fitting a blow-out panel over the inner aperture;
   opening the valve of the connecting duct between the two inner chambers;
   letting pressurized air into the chambers through the inlet;
   closing the valve, whereby each of the two inner chambers is hermetically sealed and pressurized; and
   opening the door of one of the two chambers, causing a substantially instantaneous pressure drop in the inner chamber to atmospheric pressure.

* * * * *